US012251132B2

United States Patent
O'Dea et al.

(10) Patent No.: US 12,251,132 B2
(45) Date of Patent: Mar. 18, 2025

(54) VALVE MECHANISM FOR A TROCAR, AND A TROCAR

(71) Applicant: PALLIARE LIMITED, Galway (IE)

(72) Inventors: John O'Dea, Galway (IE); Aoife O'Dea, Galway (IE)

(73) Assignee: Palliare Limited, Galway (IE)

( * ) Notice: Subject to any disclaimer, the term of this patent is extended or adjusted under 35 U.S.C. 154(b) by 940 days.

(21) Appl. No.: 17/295,557

(22) PCT Filed: Nov. 22, 2019

(86) PCT No.: PCT/IE2019/000010
§ 371 (c)(1),
(2) Date: May 20, 2021

(87) PCT Pub. No.: WO2020/105022
PCT Pub. Date: May 28, 2020

(65) Prior Publication Data
US 2022/0047302 A1 Feb. 17, 2022

(30) Foreign Application Priority Data
Nov. 22, 2018 (IE) .................................. S2018/0459

(51) Int. Cl.
*A61B 17/34* (2006.01)
*A61B 17/00* (2006.01)

(52) U.S. Cl.
CPC ...... *A61B 17/3462* (2013.01); *A61B 17/3423* (2013.01); *A61B 17/3498* (2013.01);
(Continued)

(58) Field of Classification Search
CPC ...... A61B 2017/348; A61B 2017/3464; A61B 2017/00022; A61B 2017/00017;
(Continued)

(56) References Cited

U.S. PATENT DOCUMENTS

2004/0243059 A1* 12/2004 Pajunk ............... A61B 17/3498
606/167
2008/0294114 A1 11/2008 Smith
(Continued)

FOREIGN PATENT DOCUMENTS

DE 7004051 U 7/1970
DE 102007023427 A1 11/2008

OTHER PUBLICATIONS

European Patent Office; International Search Report and Written Opinion; PCT/IE 2019/000010; May 26, 2020.

*Primary Examiner* — Jocelin C Tanner
(74) *Attorney, Agent, or Firm* — Sughrue Mion, PLLC

(57) ABSTRACT

A valve mechanism for coupling to a trocar comprises a housing having an instrument bore extending therethrough from an upstream end to a downstream end and alignable with an instrument bore of the trocar. A gate valve comprising a pair of gate elements located in the housing is operable between a closed state closing the instrument bore and an open state clear of the instrument bore. First compression springs urge the gate elements into the closed state. A pair of engagement members, which are engageable with an instrument, for example, a laparoscope in the instrument bore, and which extend into the instrument bore from respective carrier elements through guide slots. The carrier elements are coupled to operating members of the gate elements through link members for operating the gate elements (22) from the closed state to the open state as the engagement members (33) are urged downwardly in in guide slots by an instrument being entered through the instrument bore.

22 Claims, 7 Drawing Sheets

Figure 1:
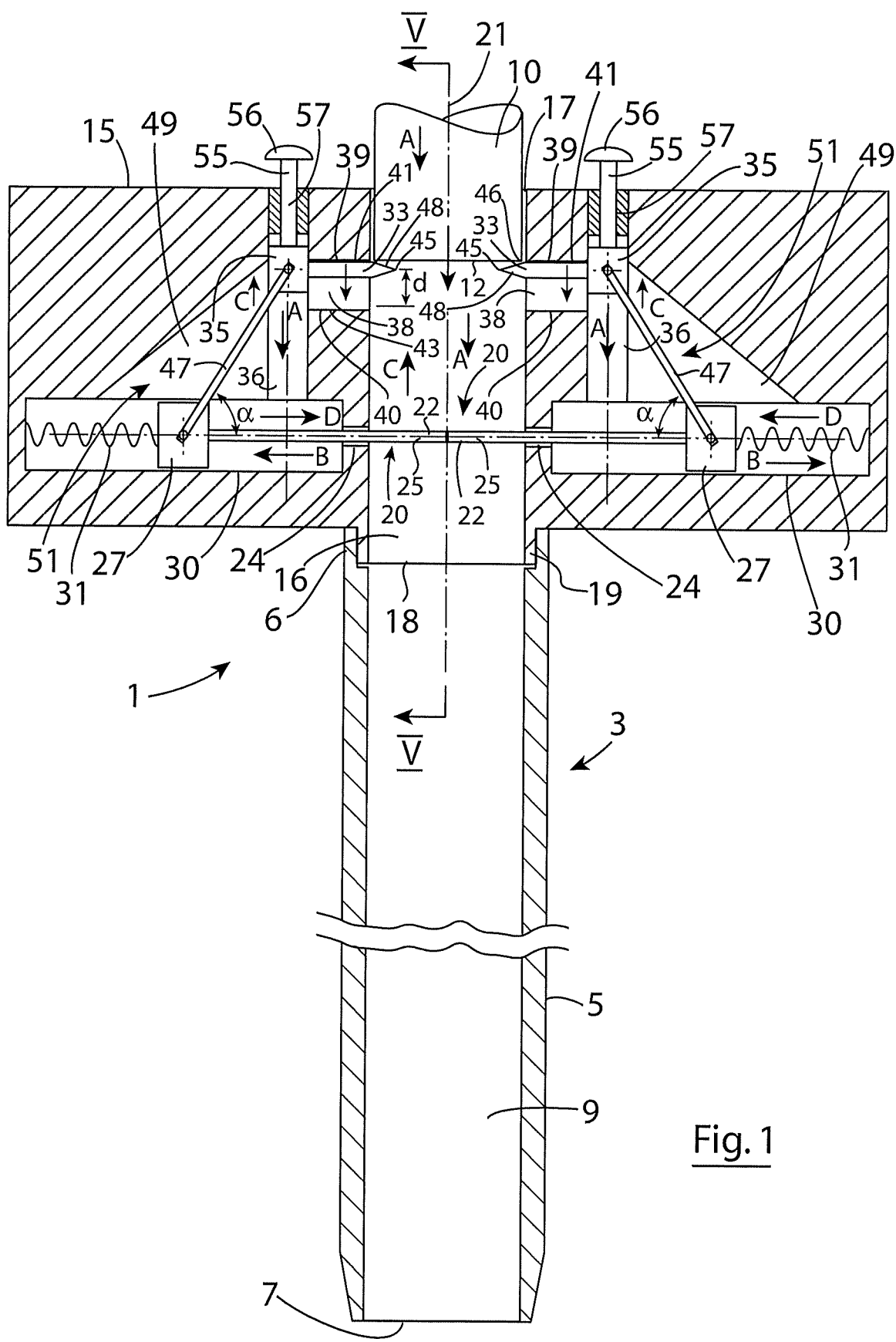

(52) U.S. Cl.
CPC ............... *A61B 2017/00017* (2013.01); *A61B 2017/00022* (2013.01); *A61B 2017/3464* (2013.01)

(58) Field of Classification Search
CPC . A61B 17/34; A61B 17/3498; A61B 17/3423; A61B 17/3462
See application file for complete search history.

(56) References Cited

U.S. PATENT DOCUMENTS

| | | | |
|---|---|---|---|
| 2017/0055942 A1 | 3/2017 | Tsuruta | |
| 2017/0086906 A1* | 3/2017 | Tsuruta | ................. A61B 90/39 |
| 2017/0215920 A1* | 8/2017 | Farin | ................. A61B 17/3468 |

* cited by examiner

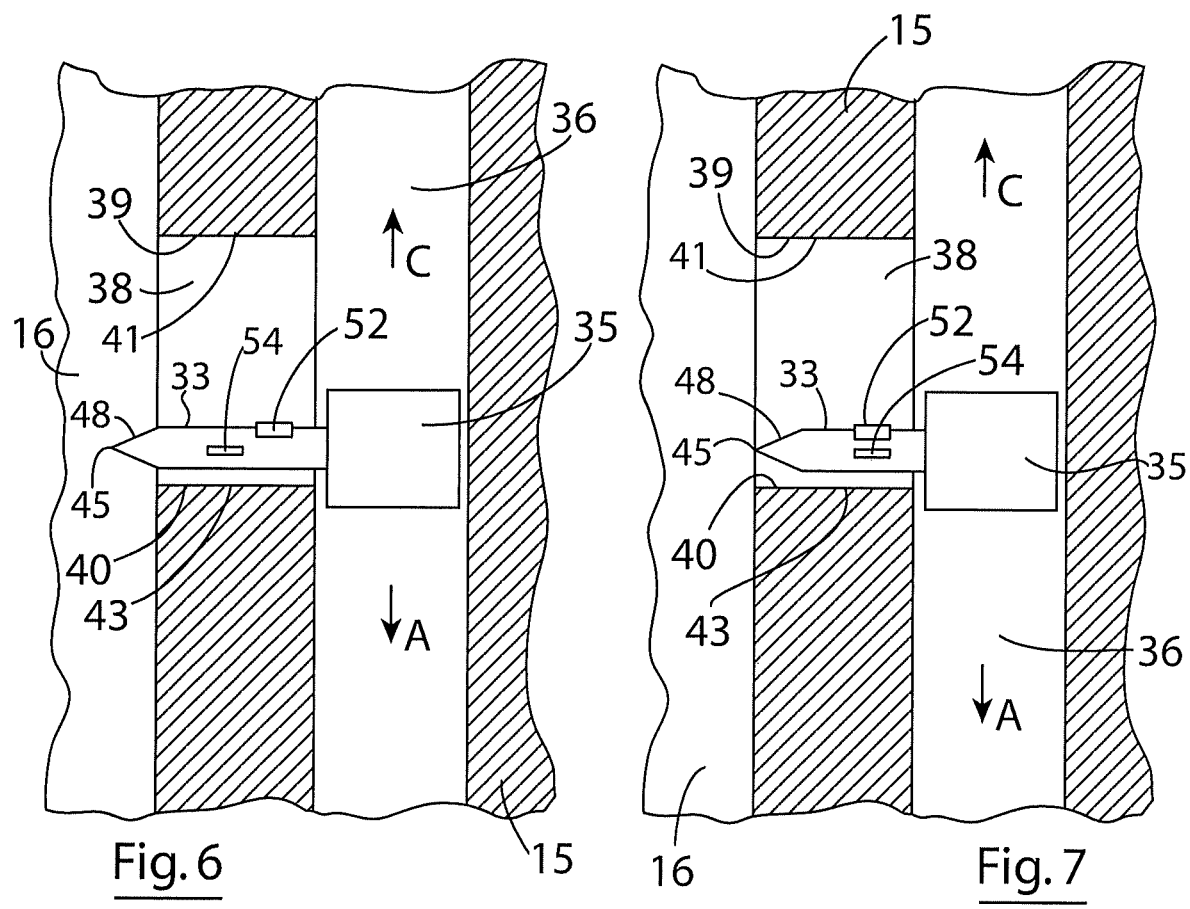
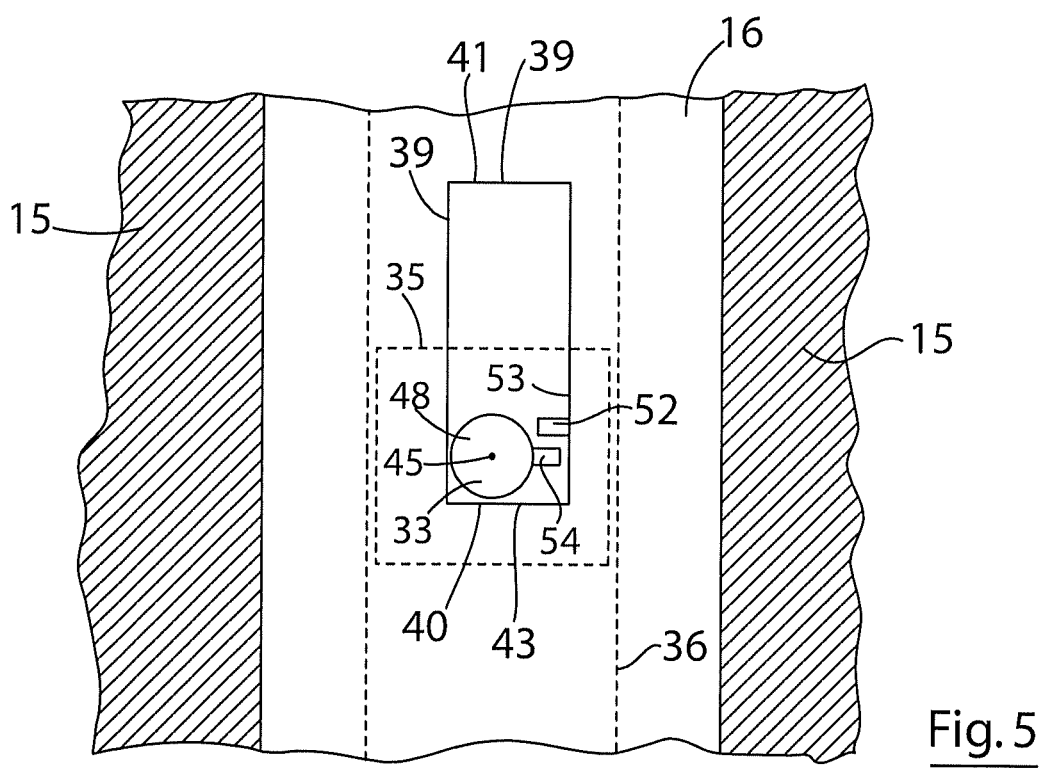
Fig. 6    Fig. 7    Fig. 5

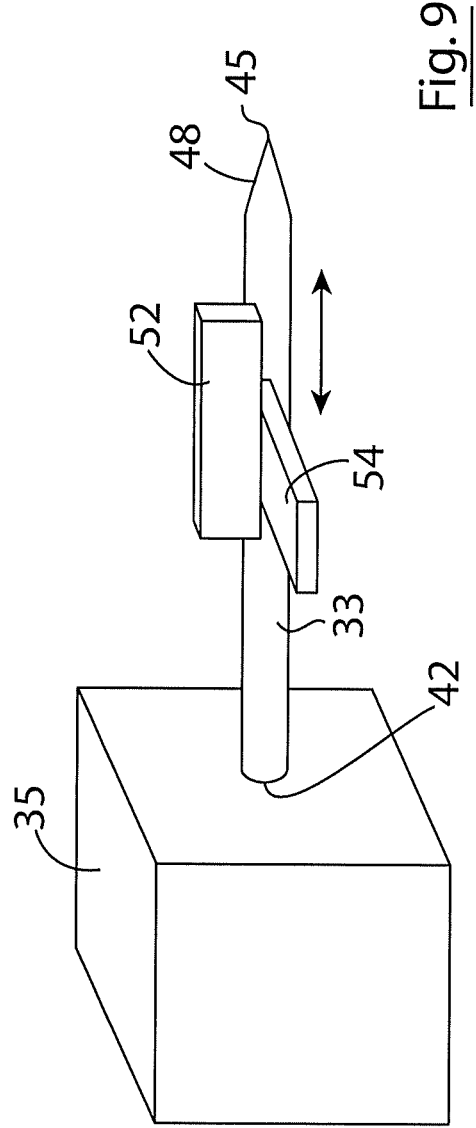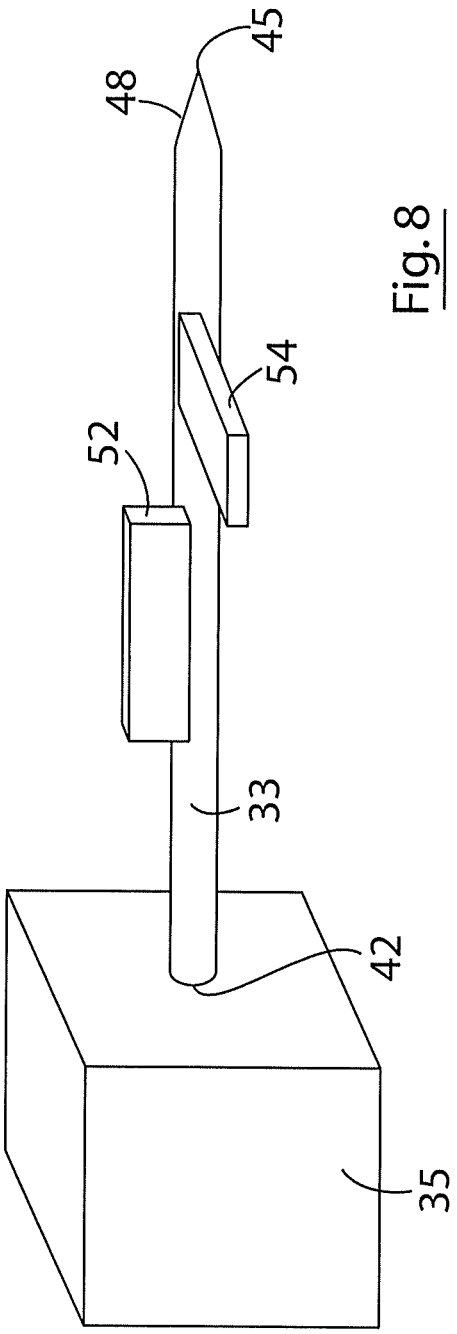

VALVE MECHANISM FOR A TROCAR, AND A TROCAR

This application claims the benefit of PCT Application PCT/IE2019/000010 filed on Nov. 22, 2019, which claims priority to Irish Application No. S2018/0459 filed on Nov. 22, 2018, the entire disclosures of which are incorporated herein by reference for all purposes.

The present invention relates to a trocar, and in particular, to a valve mechanism for a trocar, and the invention also relates to a trocar comprising the valve mechanism.

Trocars are used in laparoscopic surgery both on humans and animals. In the carrying out of laparoscopic abdominal surgery, one or more trocars are extended through the abdominal wall into the abdominal cavity in order to accommodate surgical instruments into the abdominal cavity. In order to provide an operating field for a surgeon in the abdominal cavity, the abdominal cavity is insufflated by a suitable insufflator, which pumps air or an inert gas, for example, carbon dioxide into the abdominal cavity through the trocar or other suitable instrument.

Such trocars are of tubular construction having an elongated bore extending through the trocar in order to accommodate instruments and a laparoscope into the abdominal cavity. It is important that the instrument bore extending through a trocar incorporates a sealing system for minimising the escape of insufflating gas from the abdominal cavity. Such sealing systems for sealing an instrument bore extending through a trocar, in general comprise an annular seal located in the instrument bore and extending around and into the instrument bore to bear on the instrument in the instrument bore in order to minimise the passage of insufflating gas between the seal and the instrument. However, various problems arise with such seals.

Firstly, the ability of such seals to form an adequate seal between the laparoscope and the instrument being inserted through the instrument bore of the trocar is sometimes inadequate, thus allowing uncontrolled escape of insufflating gas from the abdominal cavity.

Secondly, such seals bear on the instrument, and as the instrument is being withdrawn from the abdominal cavity, body fluids and/or surgical matter on the instruments may be deposited on the seal. This results in a serious problem. Where a laparoscope is to be entered into the abdominal cavity through the instrument bore of a trocar after an instrument has been withdrawn from the abdominal cavity through the instrument bore, and on being withdrawn deposited body fluids and/or surgical matter on the seal in the instrument bore, as the laparoscope is being inserted through the instrument bore of the trocar, the deposited body fluids and/or surgical matter on the seal transfers to the lens of the laparoscope, which is located adjacent the leading end of the laparoscope, thus occluding the lens.

These problems are unacceptable, and require to be addressed.

The present invention is directed toward providing a valve mechanism for a trocar which addresses at least some of these problems, and the invention is also directed towards a trocar comprising such a valve mechanism.

According to the invention there is provided a valve mechanism for a trocar, the valve mechanism comprising a housing, an instrument bore extending through the housing for accommodating an instrument therethrough, a valve located in the housing operable between a closed state closing the instrument bore and an open state providing access through the instrument bore, a detecting means configured to detect an instrument entering or in the instrument bore upstream of the valve, and an operating means responsive to the detecting means detecting an instrument for operating the valve between the closed and the open state.

Preferably, the operating means is responsive to the detecting means detecting movement of the instrument in the instrument bore in a downstream direction for operating the valve into the open state. Advantageously, the operating means is responsive to the detecting means detecting movement of the instrument in the instrument bore in an upstream direction for operating the valve into the closed state.

In one embodiment of the invention a first urging means is provided for urging the valve into the closed state. Preferably, the first urging means is cooperable with the operating means for urging the valve into the closed state. Advantageously, the first urging means is configured to act on the operating means. Preferably, the first urging means comprises a first resilient urging means. Ideally, the first urging means comprises a first spring, and preferably, a first compression spring.

In another embodiment of the invention the detecting means is engageable with an instrument in the instrument bore.

Preferably, the detecting means is configured to extend into the instrument bore, and is moveable in the instrument bore by the instrument.

Advantageously, the operating means is operably connected to the detecting means, and is responsive to movement of the detecting means in a downstream direction for operating the valve from the closed state to the open state.

In one embodiment of the invention the operating means is slideably mounted in the housing for operating the valve between the closed state and the open state. Preferably, the operating means is slideable transversely relative to the instrument bore.

In another embodiment of the invention a first guide means is provided for guiding the operating means transversely relative to the instrument bore. Preferably, the first guide means is configured for guiding the operating means between a first state corresponding to the closed state of the valve and a second state corresponding to the open state of the valve. Advantageously, the first guide means comprises a first guide bore extending in the housing transversely of the instrument bore.

In another embodiment of the invention the detecting means is urgeable in one or both of a generally longitudinally direction and a generally transverse direction in the instrument bore in response to movement of the instrument therein.

Preferably, the operating means is responsive to movement of the detecting means in the one or both of the generally longitudinal direction and the generally transverse direction in the instrument bore for operating the valve between the closed state and the open state.

Advantageously, the operating means is responsive to movement of the detecting means in the generally longitudinal direction in a downstream direction for operating the valve into the open state.

Preferably, the operating means is responsive to movement of the detecting means in the generally transverse direction out of the instrument bore for operating the valve into the open state.

In one embodiment of the invention a longitudinal guide means extending longitudinally along and radially from the instrument bore guides the detecting means in the longitudinal direction relative to the instrument bore. Preferably, the longitudinal guide means guides the detecting means in the transverse direction relative to the instrument bore. Advantageously, the longitudinal guide means is configured as a limit means to limit the distance of travel of the detecting means in the longitudinal direction to a predefined distance. Ideally, the longitudinal guide means terminates adjacent an upstream end thereof in an upstream limit stop and adjacent a downstream end thereof in a downstream limit stop. Preferably, the longitudinal guide means comprises a longitudinally extending guide slot.

In one embodiment of the invention the detecting means terminates in a distal end thereof defining a camming surface for engaging a leading end of the instrument so that as the instrument is urged through the instrument bore, the leading end of the instrument engages the camming surface for urging the detecting means out of the instrument bore.

In another embodiment of the invention the operating means is operably connected to the detecting means by a transmission means for transmitting movement of the detecting means in a downstream direction into movement of the operating means for operating the valve from the closed state to the open state.

In a further embodiment of the invention the transmission means is configured to proportionately increase the distance moved by the operating means in response to the distance moved by the detecting means, so that the movement of the detecting means through the predefined distance in the downstream direction results in the operating means operating the valve from the closed state to the open state.

Preferably, the detecting means extends from a carrier element. Advantageously, the detecting means is moveably mounted relative to the carrier element. Preferably, the detecting means is slideably carried in the carrier element.

In one embodiment of the invention the detecting means is moveable in the carrier element in a direction generally transversely relative to the instrument bore.

In another embodiment of the invention a second urging means is provided for urging the detecting means relative to the carrier element towards or into the instrument bore. Preferably, the second urging means comprises a second resilient urging means. Advantageously, the second urging means comprises a second spring, and preferably, a second compression spring.

In one embodiment of the invention the carrier element is slideable in a direction parallel to the instrument bore in response to the movement of the detecting means in the instrument bore.

In another embodiment of the invention a second guide means is provided for guiding the carrier element parallel to the instrument bore. Preferably, the second guide means comprises a second guide bore extending in the housing substantially parallel to the instrument bore. Advantageously, the second guide bore is spaced apart from the instrument bore.

In another embodiment of the invention the drive transmission means comprises a link member pivotally coupled to the carrier element and the operating element.

In a further embodiment of the invention the carrier element is rotatably mounted about a rotational axis, and the detecting means extends substantially radially from the carrier element into the instrument bore. Preferably, the detecting means is configured to rotate with the carrier element in response to movement of the instrument in the instrument bore. Advantageously, the rotational axis of the carrier element extends substantially perpendicularly to a plane containing the central axis of the instrument bore.

In another embodiment of the invention the transmission means comprises a gear train. Preferably, the gear train comprises a pair of gear racks, one of said gear racks being driven by the rotatable carrier element, and the other one of said gear racks being provided for transmitting drive to the operating element from the gear train. Advantageously, an intermediate transmission gear is configured to transmit drive from one of the gear racks to the other one of the gear racks.

In another embodiment of the invention a retaining means is provided for releasably retaining the detecting means in a retained state corresponding to the open state of the valve while an instrument is in the instrument bore. Preferably, the retaining means is responsive to disengagement of the detecting means by the instrument for releasing the detecting means from the retained state.

In another embodiment of the invention the detecting means comprises an engagement element configured to engage the instrument. Preferably, the engagement element of the detecting means is configured to engage a leading end of the instrument. Advantageously, the engagement element is moveable by the instrument along the predefined distance as the instrument is being urged through the instrument bore.

In another embodiment of the invention the detecting means comprises a proximity sensor for detecting an instrument entering into or in the instrument bore.

In another embodiment of the invention the operating means is responsive to a signal from the proximity sensor indicative of an instrument entering into or in the instrument bore for operating the operating means for urging the valve into the open state. Preferably, the operating means comprises a drive means for urging the valve from the closed state to the open state. Preferably, the drive means comprises an electrically powered solenoid actuator.

In another embodiment of the invention the valve comprises a gate valve.

In a further embodiment of the invention the gate valve comprises at least one gate element and the operating means is configured to operate the at least one gate element between the closed state and the open state.

Preferably, the operating means is configured to urge the at least one gate element transversely relative to the instrument bore between the closed state and the open state.

In one embodiment of the invention the gate valve comprises a pair of cooperable gate elements urgeable transversely into the instrument bore in respective opposite directions from opposite sides of the instrument bore from the open state to the closed state. Preferably, a pair of operating means is provided for operating the respective gate elements between the open state and the closed state.

In one embodiment of the invention a single detecting means is provided and each operating means is responsive to the single detecting means. Alternatively, a pair of detecting means is provided, and each operating means is responsive to the corresponding one of the pair of the detecting means.

In one embodiment of the invention the detecting means are located in the housing on respective opposite sides of the instrument bore.

In another embodiment of the invention a manually operable means is provided for operating the valve from the closed state to the open state.

Preferably, the housing is configured for releasably coupling to a trocar. Advantageously, the housing is configured for releasably coupling to an upstream end of a trocar with the instrument bore of the valve mechanism aligned with the instrument bore of the trocar.

In another embodiment of the invention a securing means is provided for securing the housing to the trocar. Preferably, the securing means comprises at least one clasp.

In one embodiment of the invention the housing of the valve mechanism is integrally formed with the trocar.

The invention also provides a trocar comprising the valve mechanism according to the invention.

The advantages of the invention are many. A particularly important advantage of the invention is achieved by virtue of the fact that the provision of the valve mechanism in conjunction with a trocar, avoids the need for including seals within the instrument accommodating bore extending through the trocar. The valve of the valve mechanism closes the instrument bore in the housing of the valve mechanism, and therefore when the valve mechanism is secured to the trocar with the respective instrument bores of the valve mechanism and the trocar aligned with each other, the valve of the valve mechanism sealably closes the instrument bore when it is in the closed state. By virtue of the fact that the detecting means is configured to detect an instrument entering into or in the instrument bore of the valve mechanism, and the detecting means is located upstream of the valve, the valve is operated from the closed state to the open state clear of the instrument bore before the instrument reaches the valve. Therefore, by the time the instrument reaches the valve, the valve is already open and is retained in the open state until the instrument has been withdrawn past the valve. Accordingly, there is no danger of any deposits of body fluids or surgical matter, which may have collected on the instrument, being deposited on the valve as the instrument is being withdrawn through the instrument bore of the valve mechanism. Accordingly, contaminating another instrument being inserted through the valve mechanism and the trocar is avoided.

Additionally, by virtue of the fact that the valve of the valve mechanism is retained in the open state while the instrument is in the instrument bore of the valve mechanism, and until the instrument has cleared the valve of the valve mechanism as the instrument is being withdrawn therefrom, similarly, there is no danger of any body fluids or surgical matter which may remain on the instrument as it is being withdrawn through the instrument bore contaminating or being deposited on the valve.

A further advantage of the invention is that while there are no instruments located in the respective instrument bores of the trocar and the valve mechanism the valve remains in the closed state, thereby sealing the instrument bore and preventing loss of insufflating fluid from the cavity into which the trocar extends.

A further advantage of the invention is that the valve is operated hands-free which leaves both of the surgeon's hands free to introduce a laparoscope or other instrument into the trocar through the valve mechanism. Additionally, the provision of the manual operated means for manually operating the valve from the closed state to the open state, permits the valve to be operated from the closed state into the fully open state manually if necessary to facilitate removal of tissue, surgical specimens and other matter through the trocar, and in turn through the valve mechanism with little or no danger of any such matter being deposited on the valve.

Additionally, there is less friction between the outer wall of a laparoscope or other instrument, and the inner surface of the instrument bore of the valve mechanism, making movement of a laparoscope or other instrument freer for a surgeon or for robotic systems, thereby allowing better movement control in the absence of such friction in the latter case.

Furthermore, the instrument bore is maintained closed by the valve unless an instrument is being passed through or is in the instrument bore. Thus, in the absence of an instrument in the instrument bore, the valve remains in the closed state, thereby preventing leaking of insufflating gas.

A further advantage of the invention is that the valve is automatically opened by the action of urging a laparoscope or other instrument into the instrument bore of the valve mechanism. Additionally, the valve remains in the open state while the laparoscope is in the instrument bore and while it is being withdrawn through the instrument bore, and furthermore, the valve remains in the open state until the leading end of the laparoscope or other instrument has passed through the valve and is well spaced apart from the valve in the upstream direction. Therefore, should contaminating matter be on the laparoscope or on the leading end of the laparoscope, there is no danger of such matter being snagged on any part of the valve. Accordingly, when the next instrument or laparoscope is being entered through the instrument bore, the valve is clean and free from body fluids and/or surgical matter, and there is therefore no danger of contaminating the next laparoscope or other instrument being urged through the valve mechanism into the trocar.

Figure 2:
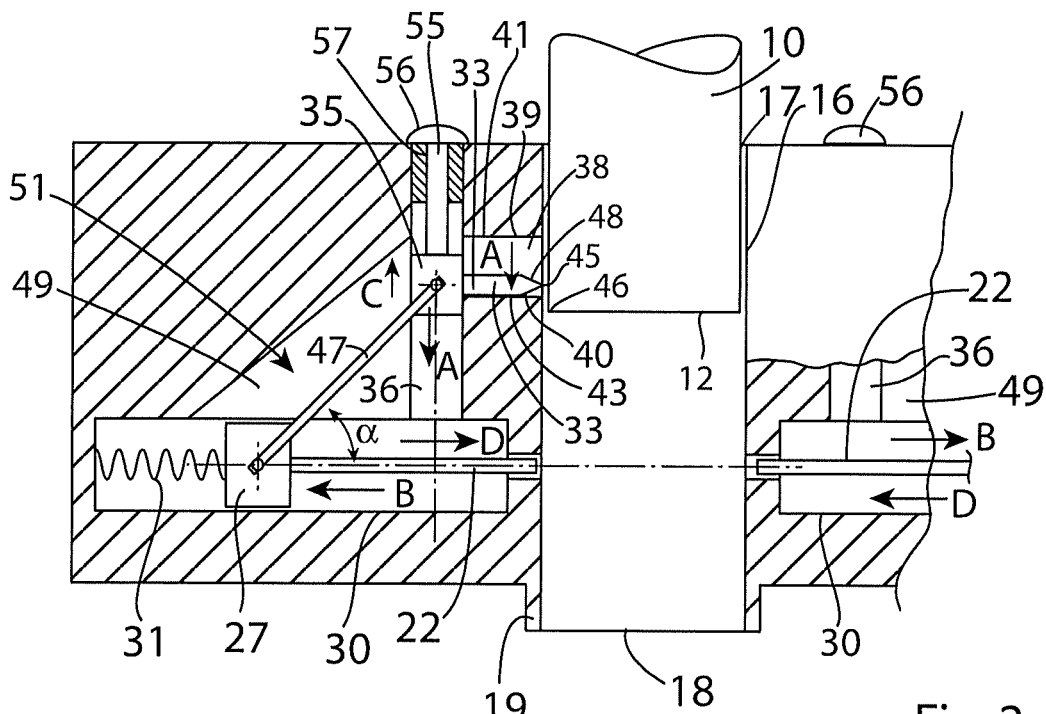
Figure 3:
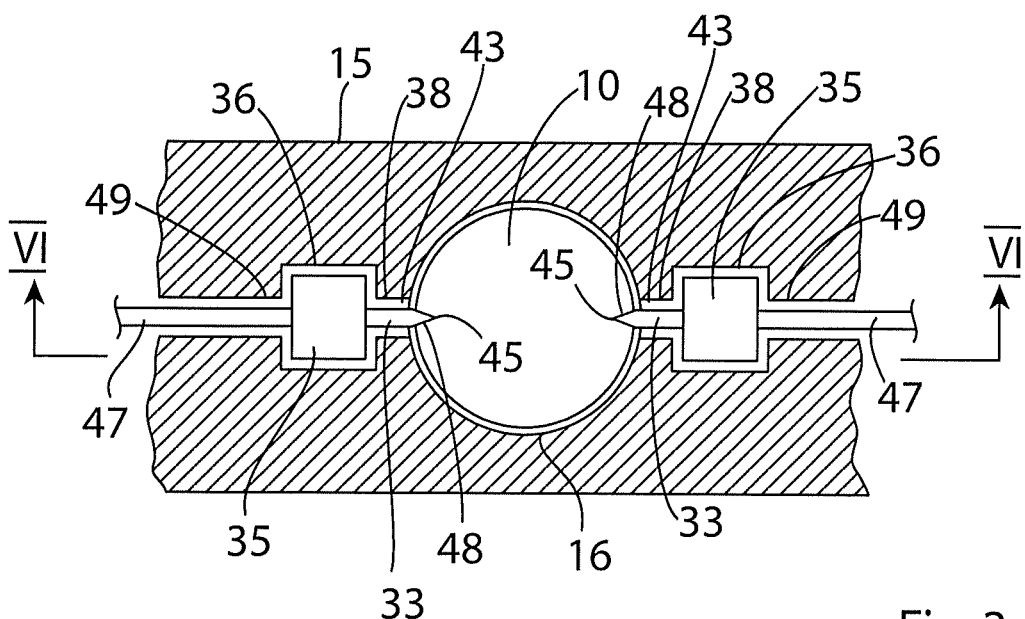
Figure 4:
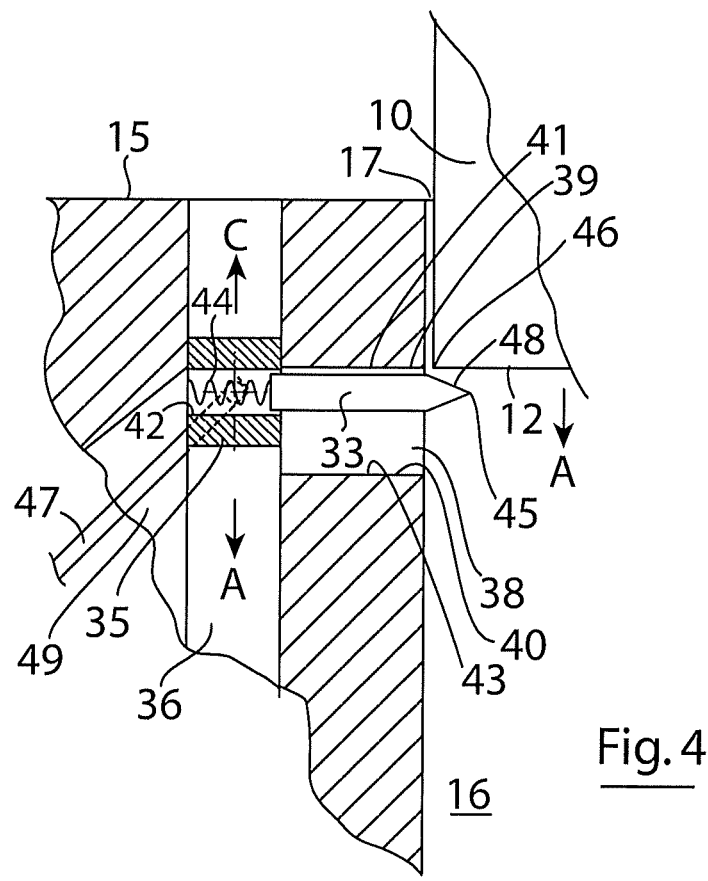
Figure 10:
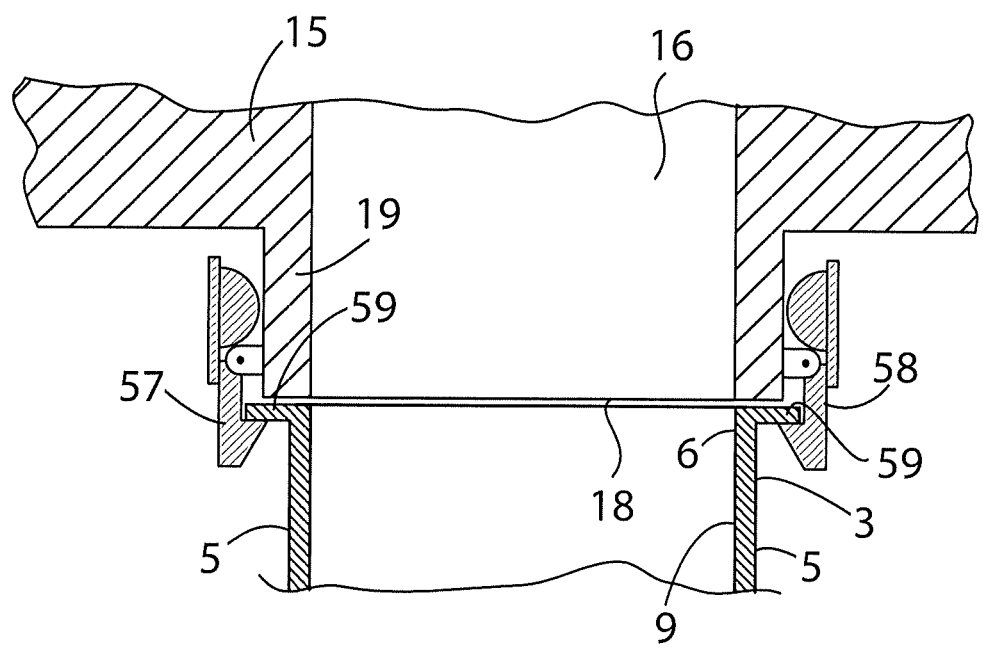
Figure 11:
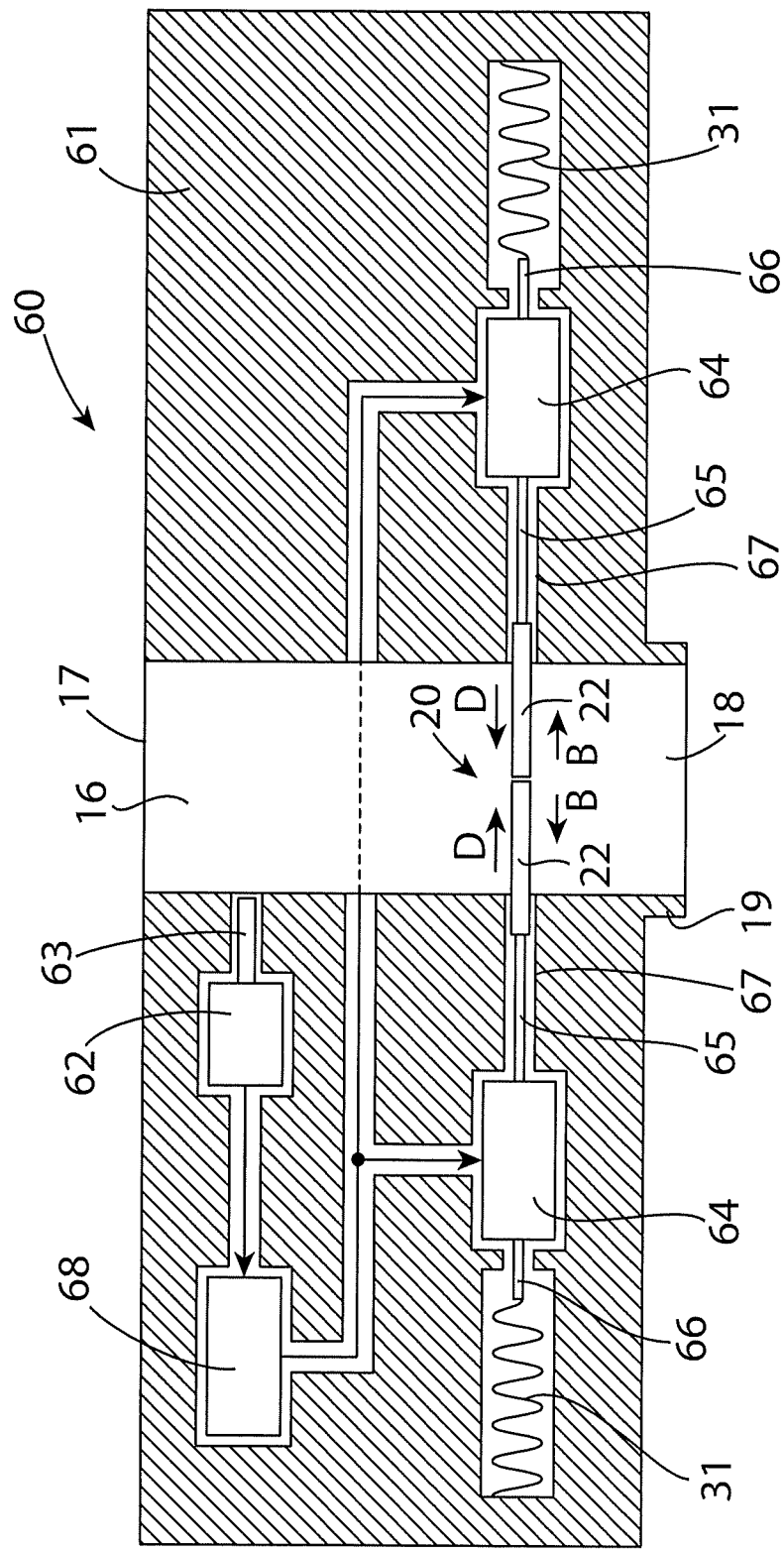
Figure 12:
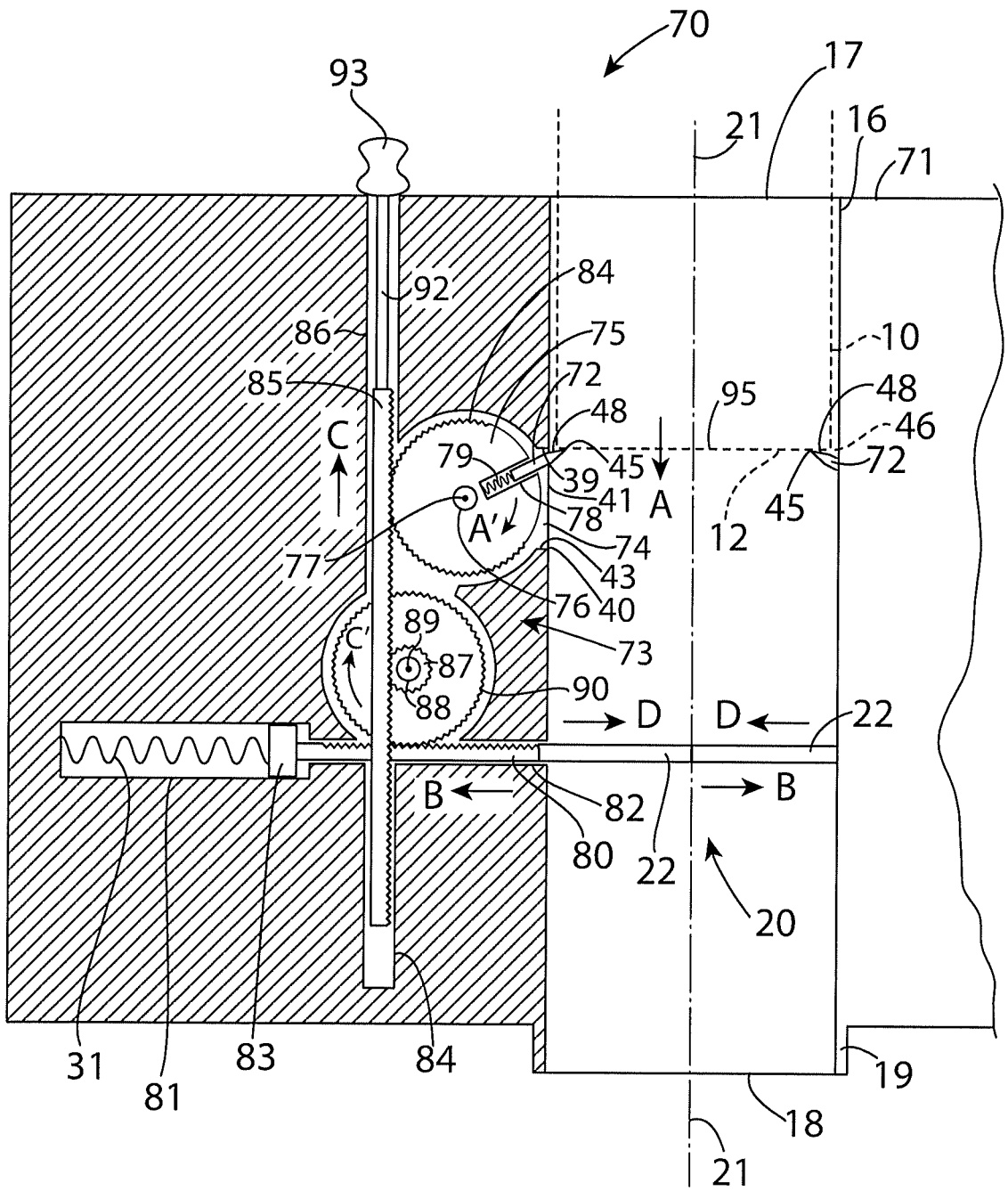

The invention will be more clearly understood from the following description of some preferred embodiments thereof which are given by way of non-limiting examples only with reference to the accompanying drawings, in which:

FIG. 1 is a partly diagrammatic cross-sectional front elevational view of a valve mechanism according to the invention illustrated coupled to a trocar, FIG. 2 is a diagrammatic front elevational view of a detail of the valve mechanism of FIG. 1, FIG. 3 is a cross-sectional top plan view of a further detail of the valve mechanism of FIG. 1, FIG. 4 is an enlarged view of a detail of the valve mechanism of FIG. 1, FIG. 5 is a cross-sectional side elevational view of a portion of the valve mechanism of FIG. 1 on the line V-V of FIG. 1, FIG. 6 is a cross-sectional front elevational view of a portion of the valve mechanism of FIG. 1 on the line VI-VI of FIG. 3 illustrating the detail of FIG. 5, FIG. 7 is a view similar to FIG. 6 of the detail of FIG. 5 in a different state to that of FIG. 6, FIG. 8 is a diagrammatic perspective view of the detail of FIG. 5 of the valve mechanism of FIG. 1 in the state of FIG. 6, FIG. 9 is a view similar to FIG. 8 of the detail of FIG. 5 of the valve mechanism of FIG. 1 illustrating the detail in the state of FIG. 7, FIG. 10 is a cross-sectional front elevational view of a detail of a valve mechanism according to another embodiment of the invention, FIG. 11 is a block representation of an operating system for use in an alternative embodiment of a valve mechanism according to another embodiment of the invention, and FIG. 12 is a half cross-sectional front elevational view of a portion of a valve mechanism according to a further embodiment of the invention.

Referring to the drawings and initially to FIGS. 1 to 9 there is illustrated a valve mechanism according to the invention indicated generally by the reference numeral 1 for releasably coupling to a trocar indicated generally by the reference numeral 3, and also according to the invention when coupled to the valve mechanism 1. The trocar 3 is of tubular constructions and comprises an elongated tubular member 5 of circular transverse cross-section extending between an upstream end 6 and a downstream end 7. The downstream end 7 of the trocar 3 may terminate in a metal or plastic sharpened, or non-bladed end. Providing the trocar 3 with a sharpened downstream end 7 facilitates entry of the trocar into the abdominal or other cavity through the abdominal wall or other wall of a subject. An elongated instrument bore 9 also of circular transverse cross-section for accommodating an instrument 10, such as, for example, a laparoscope, a surgical instrument or other instrument, a leading end 12 of which is illustrated in FIGS. 1 and 2, into the abdominal or other cavity, extends through the tubular element 5 of the trocar 3 from the upstream end 6 to the downstream end 7. Such trocars as the trocar 3 will be well known to and understood by those skilled in the art, and further description of the trocar 3 should not be required.

Turning now to the valve mechanism 1, the valve mechanism 1 comprises a housing 15 having an instrument bore 16 of circular transverse cross-section extending therethrough from an upstream end 17 to a downstream end 18, and defining a central longitudinal axis 21. The downstream end 18 of the instrument bore 16 of the housing 15 terminates in a flange 19 extending in a downstream direction from the housing 15 for coupling the valve mechanism 1 to the trocar 3. The flange 19 is engageable in the upstream end 6 of the instrument bore 9 of the trocar 3 with the instrument bore 16 of the valve mechanism 1 aligned with the instrument bore 9 of the trocar 3.

A valve, in this embodiment of the invention a gate valve 20 is provided in the housing 15 for selectively and substantially sealably closing the instrument bore 16 towards the downstream end 18 thereof. In this embodiment of the invention the gate valve 20 comprises a pair of gate elements 22 located in the housing 15, which are slideable into the instrument bore 16 through gate accommodating slots 24 formed in the housing 15. The gate accommodating slots 24 extend transversely relative to the instrument bore 16 for slideably accommodating the gate elements 22 from an open state illustrated in FIG. 2 with the gate elements 22 clear of the instrument bore 16 providing access through the instrument bore 16, to a closed state illustrated in FIG. 1 with the gate elements 22 abutting each other substantially centrally in the instrument bore 16 adjacent the central longitudinal axis 21 thereof closing the instrument bore 16. In this embodiment of the invention each gate element 22 comprises a plate member 25.

An operating means, in this embodiment of the invention, a pair of operating means, namely, a pair of operating elements 27 are located in the housing 15 on respective opposite sides of the instrument bore 16 for urging the gate elements 22 between the open state and the closed state. Each operating element 27 is connected directly to the corresponding gate element 22. The operating elements 27 are slideably mounted in respective first guide means, namely, respective first guide bores 30 which extend transversely in the housing 15 relative to the central axis 21 of the instrument bore 16 thereof on respective opposite sides of the instrument bore 16. The operating elements 27 are slideable in the corresponding first guide bores 30 between a first state illustrated in FIG. 1 with the gate elements 22 of the gate valve 20 in the closed state, and a second state illustrated in FIG. 2 with the gate elements 22 in the open state. A first urging means for urging the gate elements 22 from the open state to the closed state, in this embodiment of the invention comprises a pair of first resilient urging means provided by respective first compression springs 31. Each first compression spring 31 is located in the corresponding first guide bore 30, and acts between the corresponding operating element 27 and the housing 15 for resiliently urging that operating element 27 from the second state to the first state for in turn resiliently urging the corresponding gate element 22 from the open state to the closed state. The operation of the operating members 27 for urging the gate elements 22 between the open and closed state will be described in more detail below.

A detecting means for detecting entry into or movement of an instrument, such as the instrument 10, which may be a laparoscope or other instrument or surgical instrument, in the instrument bore 16, in this embodiment of the invention, comprises a pair of engagement elements, namely, a pair of engagement members 33 extending into the instrument bore 16 from respective opposite sides thereof. The engagement members 33 are of circular transverse cross-section and are configured for engaging the leading end of an instrument 10 in the instrument bore 16. The engagement members 33 are moveable in a downstream direction, namely, in the direction of the arrow A, in the instrument bore 16 by the leading end 12 of the instrument 10 as the instrument 10 is being urged into the instrument bore 16 from the upstream end 17 thereof, as will be described below. The operating elements 27 are responsive to the movement of the engagement members 33 in the downstream direction for operating the gate elements 22 of the gate valve 20 from the closed state to the open state, as will also be described below.

Each engagement member 33 is carried on a corresponding carrier element 35 which is slideably located in a corresponding second guide means, namely, a corresponding second guide bore 36 which extends in the housing 15 substantially parallel to the central axis 21 of the instrument bore 16, and is spaced apart from the instrument bore 16. The second guide bores 36 are located on respective opposite sides of the instrument bore 16 corresponding to the sides on which the operating elements 27 are slideably located in the first guide bores 30. Each engagement member 33 extends from the corresponding carrier element 35 to the instrument bore 16 through a corresponding longitudinally extending guide means, namely, a corresponding longitudinal guide slot 38. The longitudinal guide slots 38 extend in the housing 15 longitudinally along the instrument bore 16 and radially from the instrument bore 16 to the corresponding second guide bore 36. Each guide slot 38 extends longitudinally and parallel to the central axis 21 of the instrument bore 16 from an upstream end 39 to a downstream end 40, for accommodating longitudinal travel of the corresponding engagement member 33 parallel to the central axis 21 of the instrument bore 16 through a predefined longitudinal distance d from the upstream end 39 to the downstream end 40 of the corresponding guide slot 38. The predefined distance d of longitudinal travel of the engagement members 33 in the guide slots 38 is limited by the upstream ends 39 and the downstream ends 40 of the respective guide slots 38 which act as upstream and downstream limit stops 41 and 43, respectively.

The engagement members 33 extend from the corresponding carrier elements 35 into the instrument bore 16 to engage the leading end 12 of the instrument 10 as the instrument 10 is being urged into the instrument bore 16 from the upstream end 17 in a downstream direction. As the instrument 10 is urged in the downstream direction in the instrument bore 16, the leading end 12 of the instrument 10 engages the engagement members 33, thereby urging the engagement members 33 downwardly in the guide slots 38 through the predefined distance d from the upstream end 39 to the downstream end 40 thereof, for in turn urging the carrier elements 35 through the predefined distance d.

Each engagement member 33 is slideably carried in a carrier bore 42 in the corresponding carrier element 35. The carrier bores 42 extend into the carrier elements 35 transversely relative to the central axis 21 of the instrument bore 16, see FIG. 4. A second urging means, in this embodiment of the invention a second resilient urging means comprises a second compression spring 44 located in the carrier bore 42 of each carrier element 35. Each second compression spring 44 acts between the corresponding carrier element 35 and the corresponding engagement member 33 for urging the engagement member 33 in a direction transversely relative to the central axis 21 of the instrument bore 16 towards the instrument bore 16 with a distal end 45 of the corresponding engagement member 33 extending into the instrument bore 16, see FIG. 4.

The distal end 45 of each engagement member 33 is of conical shape to form a camming surface 48 for engaging a peripheral edge 46 of the leading end 12 of the instrument 10, so that when the engagement member 33 reaches the downstream limit stop 43 formed by the downstream end 40 of the guide slot 38, and can travel no further in the downstream direction, the action of the peripheral edge 46 of the leading end 12 of the instrument 10 on the camming surface 48 urges the engagement member 33 out of the instrument bore 16 against the action of the second compression spring 44 in the corresponding carrier element 35. This thereby allows the instrument 10 to be urged past the engagement members 33.

A transmission means, namely, a pair of transmission systems 51 are provided for transmitting movement of the respective carrier elements 35 in the second bores 36 to the corresponding operating elements 27, so that as the engagement members 33 and in turn the carrier elements 35 are urged in the downstream direction, namely, in the direction of the arrows A, the operating elements 27 are urged in the directions of the arrows B, from the first state to the second state, for in turn urging the gate elements 22 of the gate valve 20 from the closed state to the open state. In this embodiment of the invention each transmission system 51 comprises a linkage, namely, an elongated link member 47. Each link member 47 is pivotally coupled at one end to the corresponding carrier element 35, and at the other end to the corresponding operating element 27. A pair of link accommodating slots 49 extending from the corresponding first guide bores 30 and from the corresponding second guide bores 36 into the housing 15 accommodates the respective link members 47 and movement thereof as the carrier elements 35 move in the downstream and upstream directions, namely, in the directions of the arrows A and C respectively, and the operating elements 27 move between the second and first states.

The first and second compression springs 31 and 44 are selected, so that the spring forces exerted by the second compression springs 44 on the engagement members 33 and the spring forces exerted by the first compression springs 31 on the operating elements 27, is such that the first compression springs 31 yield before the second compression springs 44 yield. This allows the engagement members 33 to remain extending into the instrument bore 16 and in engagement with the leading end 12 of the instrument 10 as the instrument 10 is being urged in the downstream direction in the instrument bore 16, for in turn urging the engagement members 33 through the predefined distance d from the upstream limit stop 41 to the downstream limit stop 43. This in turn results in the operating elements 27 being urged from the first state to the second state in the directions of the arrows B against the action of the first compression springs 31, for in turn operating the valve 20 from the closed state to the open state. When the engagement members 33 have reached the downstream limit stops 43, the action of the leading end 12 of the instrument 10 on the camming surfaces 48 at the distal ends 45 of the engagement members 33 results in the second compression springs 44 yielding. The yielding of the second compression springs 44 results in the engagement members 33 being urged out of the instrument bore 16 against the action of the second compression springs 44 in the carrier bores 42 of the carrier elements 35 by the further downstream movement of the leading end 12 of the instrument 10 and its action on the camming surfaces 48 of the distal ends 45 of the engagement members 33. This, thus, permits the instrument 10 to pass though the instrument bore 16 past the engagement members 33, and through the valve 20 now in the open state, and into the instrument bore 9 of the trocar 3.

In this embodiment of the invention a pair of releaseable retaining means is provided for retaining the respective engagement members 33 in a retained state adjacent the downstream limit stops 43 when the leading end 12 of the instrument 10 has passed the respective engagement members 33 in the downstream direction, and the engagement members 33 have been urged out of the instrument bore 16 and into the guide slots 38. In this embodiment of the invention each retaining means comprises a retaining member 52 extending from a rear face 53 of the corresponding guide slot 38 just above the downstream end 40 thereof for engaging a lug 54 on the corresponding engagement member 33, see in particular FIGS. 5 to 9.

Each retaining member 52 is located in the corresponding guide slot 38 spaced apart inwardly from the instrument bore 16, so that the retaining members 52 are only engaged by the lugs 54, see FIGS. 7 and 9, when the engagement members 33 are urged out of the instrument bore 16 and fully into the guide slots 38 by the instrument 10, when the engagement members 33 have reached the downstream limit stops 43. Additionally, the relationship between the lugs 54 and the retaining members 52 is such that once the leading end 12 of the instrument 10 has passed the downstream ends 40 of the guide slots 38 travelling in the upstream direction, namely, in the direction of the arrows C, and the engagement members 33 have been urged by the second compression springs 44 towards the instrument bore 16 with the distal ends 45 thereof extending into the instrument bore 16, the lugs 54 disengage the retaining members 52, see FIGS. 6 and 8.

Once the lugs 54 have disengaged the corresponding retaining members 52, the engagement members 33 are free to follow the leading end 12 of the instrument 10, under the action of the first compression springs 31 acting through the operating elements 27, the link members 47 and the carrier elements 35, as the instrument is being withdrawn in the upstream direction through the instrument bore 16. The engagement members 33 follow the leading end 12 of the instrument 10 under the action of the first compression springs 31 until the engagement members 33 abut the upstream limit stops 41. At which stage the gate elements 22 of the gate valve 20 are in the closed state.

In this embodiment of the invention the engagement members 33 are slideably keyed in the carrier bores 42 in the corresponding carrier elements 35, in order to prevent rotation of the engagement members 33 in the carrier bores 42 of the carrier elements 35 as they slide therein. This ensures that when the engagement members 33 are abutting the downstream limit stops 43 the lugs 54 are correctly aligned beneath the corresponding retaining members 52. Thus as the engagement members 33 are being urged out of the instrument bore 16 and into the guide slots 38, the lugs 54 engage beneath the corresponding retaining members 52 for in turn retaining the engagement members 33 at the downstream ends 40 of the guide slots 38. The engagement members 33 remain in the retained state adjacent the downstream ends 40 of the guide slots 38 by the engagement action between the lugs 54 and the retaining members 52 until the leading end 12 of the instrument 10 has cleared the engagement members 33 on the withdrawal of the instrument 10 through the instrument bore 16. Once the leading end 12 of the instrument 10 has cleared the engagement members 33, the engagement members 33 are urged into the instrument bore 16 by the action of the second springs 44, and the lugs 54 disengage the retaining members 52, thereby leaving the engagement members 33 free to follow the leading end 12 of the instrument 10 as the instrument 10 is being withdrawn from the instrument bore 16.

As the engagement members 33, and in turn the carrier elements 35 are being urged through the predefined longitudinal distance d in the direction of the arrow A from the upstream end 39 to the downstream end 40 of the guide slots 38, the action of the link members 47 on the corresponding operating elements 27 urge the operating elements 27 in the directions of the arrows B against the action of the first compression springs 31 a sufficient distance to in turn operate the gate elements 22 of the gate valve 20 from the closed state to the open state with the gate elements 22 clear of the instrument bore 16.

In this embodiment of the invention the diameter of the instrument bore 16 in the housing 15 is approximately 12 mm. The predefined longitudinal distance d defined between the upstream limit stop 41 of the guide slot 38 and the downstream limit stop 43 thereof is approximately 2 mm. It has been found that the travel of the engagement members 33 and the carrier elements 35 through the predefined longitudinal distance d of 2 mm is sufficient to urge the operating elements 27 in the direction of the arrows B through a distance of 6 mm which is half the diameter of the instrument bore 16, and thus, is sufficient to operate the gate elements 22 of the gate valve 20 between the open and closed states. In this embodiment of the invention as the engagement members 33 and the carrier elements 35 are urged downwardly in the direction of the arrow A through the longitudinal distance d of 2 mm, the angle $\alpha$ between the link members 47 and the corresponding gate elements 22 reduces from an angle of 66° to 52°.

However, it will be appreciated that the distance d travelled by the engagement members 33 may be greater or less than 2 mm, and will depend on the ratio of movement required between the engagement members 33 and the operating elements 27. This is determined by the length of the link members 47, and the angle $\alpha$ which the link members 47 make with the corresponding gate elements 22 when the engagement members 33 are abutting the upstream limit stops 41 of the guide slots 38. Additionally, the distance d moved by the engagement members 33 will also be dependent on the diameter of the instrument bore, and also on whether the gate valve is provided as a single gate element gate valve, or a double gate element gate valve as in the gate valve 20 described with reference to this embodiment of the invention.

A pair of manually operable spindles 55 are slideably mounted in secondary guide bores 57 extending upwardly from second guide bores 36 for manually urging the carrier elements 35 in the direction of the arrow A, to manually operate the valve 20 from the closed state to the open state. Each manually operable spindle 55 extends through the corresponding secondary guide bore 57 into the corresponding second guide bore 36 for engaging the corresponding carrier element 35. Buttons 56 on the upper ends of the respective manually operable spindles 55 are provided for urging the spindles 55 in the direction of the arrow A for in turn operating the gate elements 22 of the gate valve 20 from the closed state to the open state.

In use, the valve mechanism 1 is connected to a trocar, for example, the trocar 3 adjacent the upstream end 6 thereof by engaging the flange 19 of the housing 15 in the instrument bore 9 of the trocar 3 adjacent the upstream end 6 thereof. With the flange 19 of the housing 15 securely engaged in the upstream end 6 of the instrument bore 9 of the trocar 3, the valve mechanism 1 is ready for use. The action of the first compression springs 31 retains the gate elements 22 of the gate valve 20 in the closed state. Additionally, the action of the first compression springs 31 through the link members 47 urge the corresponding carrier elements 35 and in turn the engagement members 33 in the upstream direction of the arrow C, and retain the engagement members 33 in engagement with the upstream limit stops 41 defined by the upstream ends 39 of the guide slots 38. The second compression springs 44 urge the distal ends 45 of the engagement members 33 into the instrument bore 16.

On introduction of an instrument 10, such as a laparoscope into the instrument bore 16 of the valve mechanism 1, and on urging the instrument 10 in the downstream direction, namely, the direction of the arrow A, through the instrument bore 16, as the leading end 12 of the instrument 10 engages the camming surfaces 48 adjacent the distal ends 45 of the engagement members 33, the engagement members 33 are urged in the downstream direction from the upstream end 39 to the downstream end 40 of the guide slots 38 through the predefined longitudinal distance d. This results in the operating elements 27 being urged transversely relative to the instrument bore 16 in the direction of the arrows B against the action of the first compression spring 31 from the first to the second states, which in turn operates the gate elements 22 from the closed state to the open state, thereby opening the gate valve 20. Further downstream movement of the instrument 10 results in the action of the leading end 12 thereof on the conical camming surfaces 48 at the distal ends 45 of the engagement members 33 urging the engagement members 33 transversely out of the instrument bore 16 and into the guide slots 38 against the action of the second compression springs 44, thereby permitting further downstream movement of the instrument 10 through the instrument bore 16, and in turn through the open gate valve 20 and into the instrument bore 9 of the trocar 3.

Once the engagement members 33 have been urged from the instrument bore 16 and into the guide slots 38, the lugs 54 of the engagement members 33 are engaged by the retaining members 52 in the guide slots 38, and thereby, the engagement members 33 are retained at the downstream ends 40 of the guide slots 38, while the instrument 10 is bearing on the distal ends 45 of the engagement members 33. The action of the instrument 10 bearing on the engagement members 33 and continuously urging the engagement members 33 into the guide slots 38 against the action of the second compression springs 44 with the engagement members 33 retained by the retaining members 52 at the downstream ends 40 of the guide slots 38, retains the valve 20 in the open state.

On withdrawal of the instrument 10, once the leading end 12 of the instrument 10 passes the downstream ends 40 of the guide slots 38, the engagement members 33 are urged into the instrument bore 16 by the action of the second compression springs 44, thereby disengaging the lugs 54 from the retaining members 52. With the lugs 54 disengaged from the retaining members 52, the engagement members 33 are free to move in the upstream direction in the guide slots 38 from the downstream ends 40 to the upstream ends 39 thereof under the action of the first compression springs 31 through the operating elements 27 and the link members 47. On further movement of the instrument 10 in the upstream direction, the engagement members 33, and in turn the carrier elements 35 follow the upstream movement of the leading end 12 of the instrument 10 under the action of the first compression springs 31, until the engagement members 33 abut the upstream limit stops 41 in the guide slots 38. As the engagement members 33 are being urged by the action of the first compression springs 31 through the operating elements 27 and the link members 47, the operating elements are being urged in the direction of the arrows D, thereby urging the gate elements 22 of the gate valve 20 from the open state to the closed state. Accordingly, when the engagement members 33 have reached the upstream ends 39 of the guide slots 38, the gate elements 22 of the gate valve 20 have been urged into the closed state. On removal of the instrument 10 from the instrument bore 16 of the valve mechanism 1, the instrument bore 16 is substantially sealed by the gate valve 20 in the closed state.

Should it be desired to use the valve mechanism on a trocar 3 to accommodate other instruments, for example, surgical instruments into the trocar 3, or should it be desired to remove matter resulting from surgery in an abdominal cavity through the trocar 3, the valve 20 may be opened manually by urging the manually operable spindles 55 by the buttons 56 in the direction of the arrow A for in turn urging the carrier elements 35 in the direction of the arrow A to operate the gate elements 22 of the gate valve 20 from the closed state to the open state. Releasing the buttons 56 of the manually operable spindles 55 results in the operating members 27 being urged by the first compression springs 31 in the direction of the arrow D for operating the gate elements 22 from the open to the closed state for in turn closing the gate valve 20.

Referring now to FIG. 10 there is illustrated an alternative coupling system for coupling the valve mechanism 1 to a trocar 3. In this embodiment of the invention a releasable securing means is provided for releasably securing the valve mechanism 1 to a trocar 3. The releasable securing means in this embodiment of the invention comprises at least two clasps 58 which are located on the flange 19 extending in a downstream direction from the housing 15 adjacent the downstream end 18 of the instrument bore 16. The clasps 58 are configured to engage and clamp onto a circumferential flange 59 extending radially outwardly from and circumferentially around the upstream end 6 of the trocar 3. The clasps 58 are arranged equi-spaced apart circumferentially around the flange 19. Although in this embodiment of the invention only two clasps 58 have been described, it is envisaged that three clasps 58 or four clasps 58 could be provided equi-spaced apart circumferentially around the flange 19. It will also be appreciated that any other suitable securing means may be provided for securing the valve mechanism 1 to the trocar 3 besides clasps.

Otherwise, the valve mechanism according to this embodiment of the invention is similar to the valve mechanism 1 described with reference to FIGS. 1 to 9, and its use and operation are likewise similar to the valve mechanism of FIGS. 1 to 9.

Referring now to FIG. 11 a valve mechanism according to another embodiment of the invention is illustrated in schematic form, and is indicated generally by the reference numeral 60. The valve mechanism 60 in principle is substantially similar to the valve mechanism 1 described with reference to FIGS. 1 to 9, and similar components are identified by the same reference numerals. The valve mechanism 60 comprises a housing 61 having an instrument bore 16 extending therethrough from an upstream end 17 to a downstream end 18, in a similar manner as the instrument bore 16 extends through the housing 15 of the valve mechanism 1.

A valve, which in this embodiment of the invention is also a gate valve 20, similar to the gate valve 20 of the valve mechanism 1 is located in the housing 60 and comprises a pair of gate elements 22 similar to the gate elements 22 of the valve mechanism 1. The gate valve 20 is operable between a closed state illustrated in FIG. 11 with the gate elements 22 substantially sealably closing the instrument bore 16, and an open state (not shown) but similar to that of the gate valve 20 of the valve mechanism 1 with the gate elements 22 withdrawn into the housing 60 from the instrument bore 16, leaving the instrument bore 16 unimpeded.

The housing 60 adjacent the downstream end 18 of the instrument bore 16 terminates in a downwardly extending flange 19 extending from the housing in a general downstream direction similar to the flange 19 of the valve mechanism 1 for similarly engaging in an instrument bore of a trocar adjacent the upstream end thereof.

In this embodiment of the invention the detecting means for detecting an instrument, for example, a laparoscope being entered into the instrument bore 16 comprises a proximity sensor 62 located in the housing 61 adjacent the instrument bore 16 towards the upstream end 17 thereof. The proximity sensor 62 is also configured for detecting the presence of an instrument in the instrument bore 16. A probe 63 extends from the proximity sensor 62 towards the instrument bore 16 for detecting an instrument in the instrument bore 16.

In this embodiment of the invention the operating means for operating each of the gate elements 22 from the closed state to the open state comprises a pair of drive means, in this case provided by respective solenoid actuators 64 located in the housing 61 for operating the respective gate elements 22 of the gate valve 20 from the closed state to the open state. A spindle 65 extending from each solenoid actuator 64 is secured to the corresponding gate element 22 of the gate valve 20, and the solenoid actuators 64 in this embodiment of the invention are configured when activated for urging the respective gate elements 22 of the gate valve 20 in the direction of the arrows B from the closed state to the open state. First guide bores 67 in the housing 61 accommodate sliding of the spindles 65 and the gate elements 22 of the gate valve 20 between the open and closed states.

A portion 66 of the spindle 65 of each solenoid actuator 64 extends from the opposite end of the solenoid actuator 64 to the end thereof from which the spindle extends to the corresponding gate element 22 of the gate valve 20. The portion 66 of the spindle 65 of each solenoid actuator 64 is coupled to a first urging means for urging the spindle 65 of the solenoid actuator 64 in the direction of the arrow D, for in turn urging the corresponding gate element 22 of the gate valve 20 into the closed state when the solenoid actuator 64 is deactivated. In this embodiment of the invention each first urging means comprises a first compression spring 31, which is similar to the first compression spring 31 of the valve mechanism 1, and is located in the housing 61. Each first compression spring 31 acts between the housing and the portion 66 of the spindle 65 for urging the spindle 65 in the direction of the arrow D, to in turn urge the corresponding gate element 22 of the gate valve 20 into the closed position.

A control circuit which also includes a power supply is located in the housing 61 and is illustrated by the block 68. The control circuit 68 reads signals from the proximity sensor 62 which are indicative of entry of an instrument into the instrument bore 16, as well as being indicative of the presence or absence of an instrument in the instrument bore 16. The solenoid actuators 64 are controlled by the control circuit 68, so that in response to an instrument being entered into the instrument bore 16 adjacent the upstream end 17 thereof or the presence of an instrument in the instrument bore 16, the control circuit 68 operates the solenoid actuators 64 into the active state for in turn urging the gate elements 22 of the gate valve 20 from the closed state to the open state and for maintaining the gate valve 20 in the open state.

On signals read from the proximity sensor 62 by the control circuit 68 being indicative of an instrument having been withdrawn past the probe 63 in the upstream direction from the instrument bore 16, the control circuit 68 deactivates the solenoid actuators 64, and the valve elements 22 of the gate valve 20 are urged into the closed state by the action of the first springs 31. The control circuit 68 retains the solenoid actuators 64 deactivated until the next instrument is detected entering the instrument bore 16. While the solenoid actuators 64 are deactivated by the control circuit 68, the gate elements 22 of the gate valve 20 are retained in the closed state by the first compression springs 31.

In this embodiment of the invention since the gate elements 22 of the gate valve 20 are operated from the closed state to the open state by the solenoid actuators 64, and are urged from the open state to the closed state by the first compression springs 31. Since the detecting means in this embodiment of the invention is provided by a proximity sensor 62 only one single proximity sensor is required. Indeed, it is also envisaged that in this embodiment of the invention the gate valve may be provided with one single gate element only, which in the closed state would substantially sealably close the instrument bore 16, and in the open state would be clear of the instrument bore 16. In cases where a single gate element gate valve is provided it will be appreciated that only one solenoid actuator and one first compression spring would be required.

Otherwise, the valve mechanism 60 and its use is substantially similar to that already described with reference to the valve mechanism 1 described with reference to FIGS. 1 to 9.

Referring now to FIG. 12 there is illustrated a valve mechanism according to another embodiment of the invention indicated generally by the reference numeral 70. The valve mechanism 70 is substantially similar to the valve mechanism 1 described with reference to FIGS. 1 to 9, and similar components are identified by the same reference numerals. The valve mechanism 70 comprises a housing 71 and an instrument bore 16 extending through the housing 71. A gate valve 20 comprising a pair of gate elements 22 similar to the gate valve 20 of the valve mechanism 1 is located in the housing 71 for selectively closing the instrument bore 16. In FIG. 12 only one half of the housing 71 is illustrated in cross-section, the other half of the housing 71 is a mirror image of the cross-sectioned half.

The main difference between the valve mechanism 70 and the valve mechanism 1 lies in the detecting means and in the transmission means for transmitting movement of the detecting means to movement of the valve elements 22. In this embodiment of the invention the detecting means comprises a pair of engagement members 72 located in the housing 71 on respective opposite sides of the instrument bore 16, as will be described below, and the transmission means comprises a pair of gear transmission systems 73 also located in the housing 71 on respective opposite sides of the instrument bore 16 for transmitting movement of the engagement members 72 to the corresponding gate elements 22 of the gate valve 20 for operating the gate elements 22 between the open and the closed states.

Each engagement member 72 is carried in a corresponding carrier element, which in this embodiment of the invention comprises a cylindrical carrier element 75 which is rotatably mounted in the housing 71 on a first shaft 76 about a first rotational axis 77. The first rotational axis 77 of each carrier element 75 extends perpendicularly to a plane containing the central axis 21 defined by the instrument bore 16. A guide slot 74 extending into the housing 71 from the instrument bore 16 accommodates the corresponding engagement member 72 from the corresponding carrier element 75 into the instrument bore 16.

Each engagement member 72 is slideable in a corresponding carrier bore 78 radially extending in the carrier element 75. A second urging means, in this embodiment of the invention a second compression spring 79 is located in the carrier bore 78 of each carrier element 75 acting between the carrier element 75 and the engagement member 72 for resiliently urging the engagement member 72 into the instrument bore 16 through the corresponding guide slot 74 for engaging the leading end 12 of an instrument 10, such as, for example, a laparoscope being urged in a downstream direction into the instrument bore 16 from the upstream end 17 thereof. Each guide slot 74 extends longitudinally a predefined distance d from an upstream end 39 to a downstream end 40 which define upstream and downstream limit stops 41 and 43, respectively, for limiting the longitudinal travel of the corresponding engagement member 72 in the upstream and downstream directions.

Turning now to the gate valve 20, an operating means for operating the gate elements 22 between the open state and closed state comprises respective first gear racks 80 which are connected to the respective gate elements 22 of the gate valve 20. Each first gear rack 80 is slideably mounted in the housing 71 in a first guide means, namely, a first guide bore 82 which extends transversely relative to the instrument bore 16 for urging the corresponding gate element 22 of the gate valve 20 between the open and closed states.

A first urging means, in this embodiment of the invention a first compression spring 31, which is similar to the first compression springs 31 of the valve mechanism 1, is located in the housing 71 in an extension bore 81 extending from the first guide bore 82, and acts on an end element 83 located at the end of the first gear rack 80 opposite to the end thereof to which the first gear rack 80 is connected to the corresponding gate element 22. Each first compression spring 31 acts between the housing 71 and the end element 83 of the corresponding first gear rack 80 for urging the corresponding gate element 22 into the closed state.

The gear transmission systems 73 which will now be described transmits drive between the movement of the respective engagement members 72 and the corresponding gate elements 22. Gear teeth 84 are provided on each carrier element 75 over approximately 180° of the carrier element 75 for cooperating with a corresponding elongated second gear rack 85. Each second gear rack 85 is slideably mounted in a corresponding second guide bore 86 formed in the housing 71 and extending parallel to the instrument bore 16, so that as the corresponding carrier element 75 is being rotated in the direction of the arrow A' by the engagement member 72 on engagement by the leading end 12 of the instrument 10, the second gear rack 85 is urged in the second guide bore 86 upwardly in an upstream direction, namely, in the direction of the arrow C. Each second gear rack 85 is engageable with a corresponding first intermediate gear 87 which is mounted fast on a corresponding second shaft 88 rotatably mounted in the housing 71 about a second rotational axis 89 extending parallel to the first rotational axis 77 of the carrier element 75. A second intermediate gear 90 of diameter greater than the diameter of the first intermediate gear 87 is also mounted fast on the corresponding second shaft 88 and is rotatable with the corresponding first intermediate gear 87. The second intermediate gear 90 of each gear transmission system 73 is in driving engagement with the corresponding first gear rack 80, so that on rotation of the second intermediate gear 90 about the second rotational axis 89, the corresponding gate element 22 of the gate valve 20 is operated between the open state and the closed state.

Accordingly, on rotation of the carrier elements 75 in the direction of the arrow A' resulting from the engagement members 72 being urged in the downstream direction, namely, in the direction of the arrow A by the leading end 12 of the instrument 10 being urged into the instrument bore 16 in the downstream direction, the second gear racks 85 are urged in an upstream direction, namely, in the direction of the arrow C, which in turn results in rotation of the first and second intermediate gears 87 and 90 in the direction of the arrow C'. This, in turn results in the first gear racks 80 being urged in the direction of the arrow B, for in turn urging the corresponding gate elements 22 of the gate valve 20 into the open state.

As the instrument 10 is urged further in the downstream direction through the instrument bore 16, by the time the leading end 12 of the instrument 10 has reached the downstream ends 40 of the guide slots 74 in the instrument bore 16, the engagement members 72 have been urged against the downstream limit stops 43 of the guide slots 74, and thereby rotation of the engagement members 72 terminates. However, at this stage the conical camming surfaces 48 adjacent the distal ends 45 of the engagement members 72 remain projecting slightly into the instrument bore 16. On further movement of the instrument 10 in the downstream direction through the instrument bore 16, the leading end 12 of the instrument 10 acts on the camming surfaces 48 at the distal ends 45 of the engagement members 72, thereby, urging the engagement members 72 into the corresponding carrier bores 78 in the carrier elements 75 against the action of the second compression springs 79. This, permits the instrument 10 to be urged through the instrument bore 16 past the engagement members 72. At this stage the gate elements 22 of the gate valve 20 are in the open state, and accordingly, the instrument 10 may then be urged through the instrument bore 16 of the valve mechanism 70 and in turn into the instrument bore 9 of the trocar 3.

For so long as the instrument 10 is located in the instrument bore 16 the action of the instrument 10 bearing on the engagement members 72, and the action of the second compression springs 79 urging the engagement members 72 into engagement with the instrument 10 results in the engagement members 72 being retained abutting the downstream limit stops 43 of the guide slots 74, thereby retaining the gate elements 22 of the gate valve 20 in the open state.

On withdrawal of the instrument 10 through the instrument bore 16, on the leading end 12 of the instrument 10 passing the downstream ends 40 of the guide slots 74, the engagement members 72 are urged by the second compression springs 79 into the instrument bore 16. As the leading end 12 of the instrument 10 is urged further in the instrument bore 16 in the upstream direction, the spring urging forces of the first compression springs 31 acting on the first gear racks 80 result in the first gear racks 80 being urged in the directions of the arrow D. This in turn results in the engagement members 72 following the leading end 12 of the instrument 10 in the upstream direction, which in turn permits the second compression springs 31 to urge the corresponding gate elements 22 from the open state towards the closed state. The engagement members 72 follow the leading edge 12 of the instrument 10 as the instrument 10 is being withdrawn in the upstream direction through the instrument bore 16. Once the engagement members 72 abut the upstream limit stops 41 defined by the upstream ends 39 of the guide slots 74, further rotation of the carrier elements 75 is prevented, and at this stage the corresponding gate elements 22 of the gate valve 20 are in the closed state. When the engagement members 72 are abutting the upstream limit stops 41, the distal ends 45 of the engagement members 72 project into the instrument bore 16 for engaging the next instrument or laparoscope being entered into the instrument bore 16. While the engagement members 72, the carrier elements 75 and the first and second gear racks 80 and 85 and the first and second intermediate gears 87 and 90 of the transmission systems 73 have been illustrated on only one side of the instrument bore 16, it will be readily understood by those skilled in the art that engagement members 72, carrier elements 75 and first and second gear racks 80 and 85 and first and second intermediate gears 87 and 90 of the transmission systems 73 will be provided in the housing 15 on respective opposite sides of the instrument bore 16 for operating the respective gate elements 22 of the gate valve 20.

Manually operable spindles 92 extend upwardly from the second gear racks 85 through the second guide bores 86 to the upstream end 17 of the housing 71. Hand grip knobs 93 mounted fast on the manually operable spindles 92 are provided for manually operating the second gear racks 85 in the direction of the arrow C for in turn manually operating the corresponding gate elements 22 of the gate valve 20 into the open state.

Otherwise, the valve mechanism 70 and its operation is similar to that of the valve mechanism 1.

While the embodiments of the valve mechanisms according to the invention have been described with specific types of detecting means and specific types of operating means, any other suitable type of detecting means and operating means may be provided. Needless to say, any other suitable transmission means for transmitting movement of the detecting means to the operating means may be provided besides those described. For example, instead of a transmission means being provided by cooperating gears and gear racks as in the case of the valve mechanism 70, a transmission means comprising cooperating gear wheels only could also be provided.

While the angular movement α between the link members 47 and the corresponding gate elements 22 of the gate valve 20 as the engagement members 33 and in turn the carrier elements 35 are being moved through the distance d from the upstream ends 39 to the downstream ends 40 of the guide slots 38 has been described as being an angle of 14°, the angle α as the engagement members 33 are being moved through the predefined distance d from the upstream ends 39 to the downstream ends 40 of the guide slots 38 may vary from 30° to 85° when the gate valve 20 is in the closed state, and 10° to 60° when the gate valve 20 is in the open state.

It will also be appreciated that the distance between the downstream ends 40 of the guide slots 38 and the gate elements 22 of the gate valve 20 will always be sufficient to ensure that the gate valve 20 is in the fully open state before the instrument, for example, a laparoscope reaches the gate valve 20.

While the valves in the embodiments of the invention described have been described as comprising a gate valve, any other suitable valve may be provided. Indeed, it will be appreciated that where the valve is provided as a gate valve, the gate valve may be of the type which would comprise a single gate element only which would operate from one side of the instrument bore 16 in the open state to the other side of the instrument bore 16 in the closed state. Further, it is envisaged that the valve may be provided by a ball valve, and in which case, it is envisaged that the ball valve would be rotated through 90° from the open state to the closed state by a gear transmission system which would transmit a linear or a rotational movement of the detecting means to rotational movement of the ball valve.

In the case of a ball valve, or a single gate element gate valve, only one detecting means, for example, one engagement member and one carrier element would be required, and transmission of movement from the engagement member and the carrier element to the valve would be through a single transmission system. In cases where the valve of the valve mechanism 70 described with reference to FIG. 12 is replaced with a ball valve, the rotational movement of a single engagement member 72 about the first rotational axis 77 would be transmitted to rotational movement of the ball valve through a gearing system, such as a series of gear wheels or a rack and pinion transmission system, or a combination of both.

It is also envisaged that a single detecting means would be sufficient in the case of a gate valve with a pair of gate elements, and in which case suitable transmission means would be provided for transmitting the movement of the single detecting means to the two gate elements of the gate valve.

While the engagement members have been described as being slideable in the corresponding carrier elements 35, or the carrier elements 75, in certain cases, it is envisaged that the engagement members may be fixed relative to the carrier elements.

While specific transmission systems have been described for transmitting movement from the detecting means to the valve, it will be readily apparent to those skilled in the art that any suitable transmission means may be provided.

Needless to say, any other construction of detecting means besides an engagement member and a carrier element may be provided. It will also of course be appreciated that any other suitable retaining means for retaining the engagement members adjacent the downstream ends of the guide slots 38 may be provided.

It will be appreciated that while the second gear racks 85 of the valve mechanism 70 have been described as being located on the side of the first and second rotational axes 77 and 89 remote from the instrument bore 16, the second gear racks 85 may be located on the side of the first and second rotational axes 77 and 89 proximal to the instrument bore 16. This would have the advantage that when manually operating the valve from the closed to the open state, the knobs 93 instead of being pulled in the upstream direction of the arrows C would be pushed in the downstream direction, namely, the direction of the arrow A.

While the instrument bore in the valve mechanisms has been described as being of circular transverse cross-section, the instrument bore may be of any suitable cross-section, for example, the instrument bore may be of square cross-section, hexagonal cross-section, or any other suitable transverse cross-section. Needless to say, the instrument bore through the trocar may be of the same or different transverse cross-section to that of the instrument bore extending through the valve mechanism.

It will of course be appreciated that while the various embodiments of the valve mechanism according to the invention have been described with specific components, components from some of the valve mechanisms of the embodiments of the invention may be incorporated into other ones of the valve mechanisms according to the invention.

While the valve mechanisms according to the invention have been described as being configured with an instrument bore for accommodating an instrument, such as a laparoscope or a surgical instrument therethrough, it will be appreciated that the instrument bore may accommodate any surgical or other instruments therethrough, and needless to say, the instrument bore of the valve mechanisms according to the invention may accommodate any instrument, surgical instrument, laparoscope or any other device or element therethrough to the instrument bore of a trocar.

The invention claimed is:

1. A valve mechanism for a trocar, the valve mechanism comprising:
   a housing,
   an instrument bore extending through the housing for accommodating an instrument therethrough,
   a valve located in the housing operable between a closed state closing the instrument bore and an open state providing access through the instrument bore,
   a detecting element configured to detect an instrument entering or in the instrument bore upstream of the valve,
   an operating element responsive to the detecting element detecting an instrument for operating the valve between the closed state and the open state, and
   a first urging element configured to act on the operating element for urging the valve into the closed state.

2. The valve mechanism as claimed in claim 1 in which the operating element is slideable transversely relative to the instrument bore.

3. The valve mechanism as claimed in claim 1 in which a first guide element is provided for guiding the operating element transversely relative to the instrument bore.

4. The valve mechanism as claimed in claim 1 in which the detecting element is urgeable in one or both of a generally longitudinally direction and a generally transverse direction in the instrument bore in response to movement of the instrument therein.

5. The valve mechanism as claimed in claim 4 in which the operating element is responsive to movement of the detecting element in the generally transverse direction out of the instrument bore for operating the valve into the open state.

6. The valve mechanism as claimed in claim 4 in which a longitudinal guide element extending longitudinally along and radially from the instrument bore guides the detecting element in the longitudinal direction relative to the instrument bore.

7. The valve mechanism as claimed in claim 1 in which the operating element is operably connected to the detecting element by a transmission system for transmitting movement of the detecting element in a downstream direction into movement of the operating element for operating the valve from the closed state to the open state.

8. The valve mechanism as claimed in claim 1 in which the detecting element extends from a carrier element.

9. The valve mechanism as claimed in claim 8 in which the detecting element is moveably mounted relative to the carrier element.

10. The valve mechanism as claimed in claim 8 in which a second urging element is provided for urging the detecting element relative to the carrier element towards or into the instrument bore.

11. The valve mechanism as claimed in claim 8 in which the carrier element is slideable in a direction parallel to the instrument bore in response to the movement of the detecting element in the instrument bore.

12. The valve mechanism as claimed in claim 8 in which a second guide element is provided for guiding the carrier element parallel to the instrument bore.

13. The valve mechanism as claimed in claim 8 in which the carrier element is rotatably mounted about a rotational axis, and the detecting element extends substantially radially from the carrier element into the instrument bore.

14. The valve mechanism as claimed in claim 13 in which the detecting element is configured to rotate with the carrier element in response to movement of the instrument in the instrument bore.

15. The valve mechanism as claimed in claim 1 in which a retaining element is provided for releasably retaining the detecting element in a retained state corresponding to the open state of the valve while an instrument is in the instrument bore.

16. The valve mechanism as claimed in claim 1 in which the valve comprises a gate valve having at least one gate element, and the operating element is configured to urge the at least one gate element transversely relative to the instrument bore between the closed state and the open state.

17. The valve mechanism as claimed in claim 1 in which a manually operable element is provided for operating the valve from the closed state to the open state.

18. A trocar comprising the valve mechanism as claimed in claim 1.

19. A valve mechanism for a trocar, the valve mechanism comprising:
a housing,
an instrument bore extending through the housing for accommodating an instrument therethrough,
a valve located in the housing operable between a closed state closing the instrument bore and an open state providing access through the instrument bore,
a detecting element configured to detect an instrument entering or in the instrument bore upstream of the valve, the detecting element being urgeable in a generally longitudinal direction in the instrument bore in response to movement of the instrument therein, and
an operating element responsive to the detecting element detecting an instrument for operating the valve between the closed state and the open state.

20. The valve mechanism as claimed in claim 19 in which a first urging element is provided for urging the valve into the closed state.

21. The valve mechanism as claimed in claim 20 in which the first urging element is configured to act on the operating element.

22. A valve mechanism for a trocar, the valve mechanism comprising:
a housing,
an instrument bore extending through the housing for accommodating an instrument therethrough,
a valve located in the housing operable between a closed state closing the instrument bore and an open state providing access through the instrument bore,
a detecting element configured to detect an instrument entering or in the instrument bore upstream of the valve,
a carrier element rotatably mounted about a rotational axis, the detecting element extending substantially radially from the carrier element into the instrument bore, and
an operating element responsive to the detecting element detecting an instrument for operating the valve between the closed state and the open state.

\* \* \* \* \*